United States Patent [19]

Vollweiler

[11] Patent Number: 4,949,582
[45] Date of Patent: Aug. 21, 1990

[54] LIQUID SAMPLER

[76] Inventor: Arthur R. Vollweiler, 105 Harrison, American Falls, Id. 833211

[21] Appl. No.: 319,541

[22] Filed: Mar. 6, 1989

[51] Int. Cl.$^5$ .............................................. G01N 1/12
[52] U.S. Cl. ............................................... 73/804.63
[58] Field of Search ........... 73/864.63, 864.66, 864.67, 73/864.65

[56] References Cited

U.S. PATENT DOCUMENTS

| | | | |
|---|---|---|---|
| 1,759,444 | 5/1930 | Dunn et al. | 73/864.65 |
| 2,593,830 | 4/1952 | Baker | 73/864.65 |
| 2,622,435 | 12/1952 | Lucas et al. | 73/864.65 X |
| 3,055,764 | 9/1962 | Pryor et al. | 73/864.63 |
| 4,367,657 | 1/1983 | Ward | 73/864.65 X |
| 4,590,810 | 5/1986 | Hunkin et al. | 73/864.63 |
| 4,625,574 | 12/1986 | Robbins | 73/864.63 |

FOREIGN PATENT DOCUMENTS 34676 9/1981 European Pat. Off. ......... 73/864.65

OTHER PUBLICATIONS

AMS Sampling Brochure; 16 pages & covers; published by Oct. 1989.

*Primary Examiner*—Tom Noland
*Attorney, Agent, or Firm*—K. S. Cornaby

[57] ABSTRACT

A device for sampling liquid and semi-liquid materials which comprises a container with a top and end cap, the container being filled through an opening in the top cat which is closed by a valve manually or electrically operated by the user. After filling, the container may be capped with permanent caps for transportation, or the container may be emptied into another container through the end cap which is fitted with a spring biased valve allowing discharge of the contents.

12 Claims, 6 Drawing Sheets

LIQUID SAMPLER

BACKGROUND OF THE INVENTION

Many industries and disciplines require that testing be done of liquid and semi-liquid substances. For example, waters in lakes or streams may be tested, toxic substances in land fills or dumps may be tested, and oil, gas or mud samples in the fuels industry may require testing. The uses of sampling devices in various industries are innumerable, and these present only a few examples. Sampling apparatuses have been designed and adapted for many such uses. The invention herein presents a portable and easily operated apparatus for sampling many types of liquid and semi-liquid materials, including toxic wastes. It can be used at any depth and has the significant advantage of being stable at any instance of use; that is, unlike other sampling apparatuses which require a violent jerk to open the sampling container, the invention herein may be easily opened with a simple hand movement thereby assuring stability to the sampling procedure.

SUMMARY OF THE INVENTION

The liquid sampler disclosed herein is comprised of a hollow cylindrical container to which a cap is attached at the lower end. An upper cap is attached to the container which has an opening therein. A valve, actuated by either manual, electrical, hydraulic, pressurized air, or other means, covers the opening in the upper cap. As the container is lowered into the substance to be tested, the valve is closed. A monitor on the apparatus indicates to the user when the surface of the substance has been reached. This provides important information to the user when testing in wells or crevices. When critical depth is reached, the operator opens the valve and the sampling material fills the container through the cap opening. The valve is then closed and the sampler is removed from the testing medium. A manual system or an electric system has the capability of taking composite samples throughout the medium being sampled. This is accomplished by being able to open and close the ball valve as many times as necessary to fill the container.

After extraction from the testing medium, the upper cap of the sampler may be removed and replaced with a closed cap for transportation. Alternatively, multiple containers may be joined together with threaded coupling caps which permits larger volume samples to be taken and also provides for the individual containers to be capped to maintain each container's contents separately from the other containers. In one embodiment, the end cap is fitted with a spring biased rod which operates to release a valve in the end cap; the contents of the container may thus be emptied into another container by releasing the valve in the end cap. In this manner, the contents may be emptied from the container without the operator ever touching the testing material. In another embodiment, the end cap is comprised of a two-stage interlocking cap which, when the two stages are adjusted to the greatest distance apart, maintains the spring biased rod and valve in a closed position. In this embodiment, the contents of the container will not be accidentally emptied should the spring biased rod be disrupted in movement. In any embodiment described, the end caps are easily cleaned and decontaminated.

The container may be made of stainless steel, brass, aluminum, plastic, or other suitable material. The containers may be made in varying sizes and shapes to accommodate the conditions of the testing medium, sampling conditions, or amount of testing material needed. The end cap may similarly be made of stainless steel, other metal, plastic or plastic-like materials, or any other suitable material.

The invention herein has the advantage over other sampling devices of allowing the operator to open and close the valve with a simple movement of the hand. In other sampling devices, a violent force must be used to open the valve, and when once opened, the valve is not recloseable. This and other advantages of this new invention will become more apparent in the discussion which follows.

DETAILED DESCRIPTION OF THE PREFERRED EMBODIMENT

Figure 1:
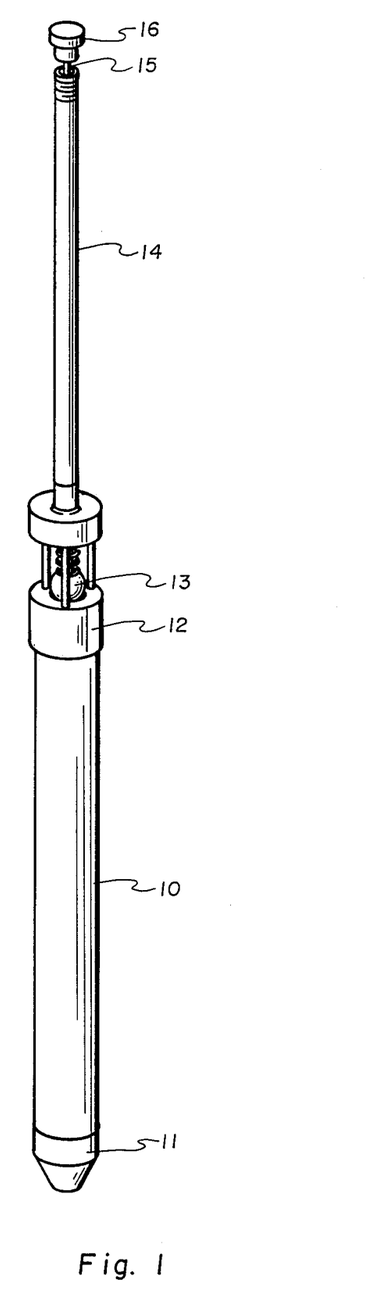
FIG. 1 is a plan view of the invention illustrating the manually operated valve embodiment.
Figure 2:
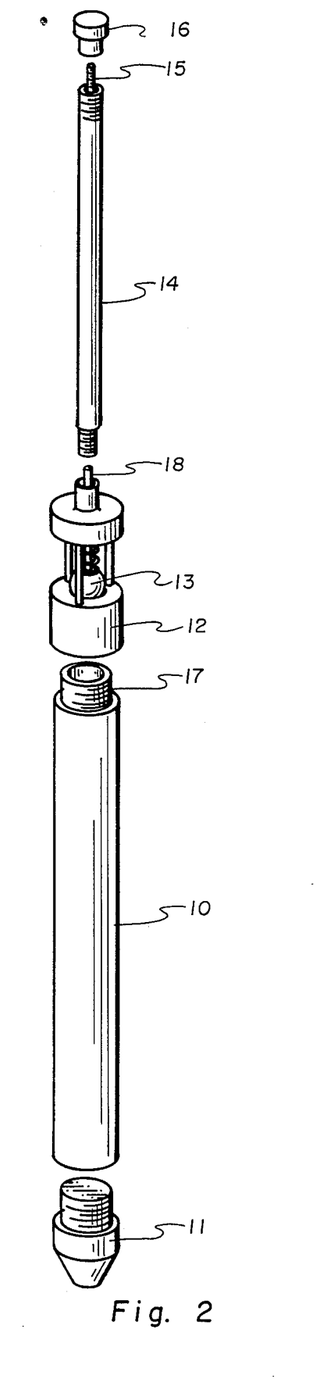
FIG. 2 is a partially exploded plan view of the invention illustrating the manually operated valve embodiment.
Figure 3:
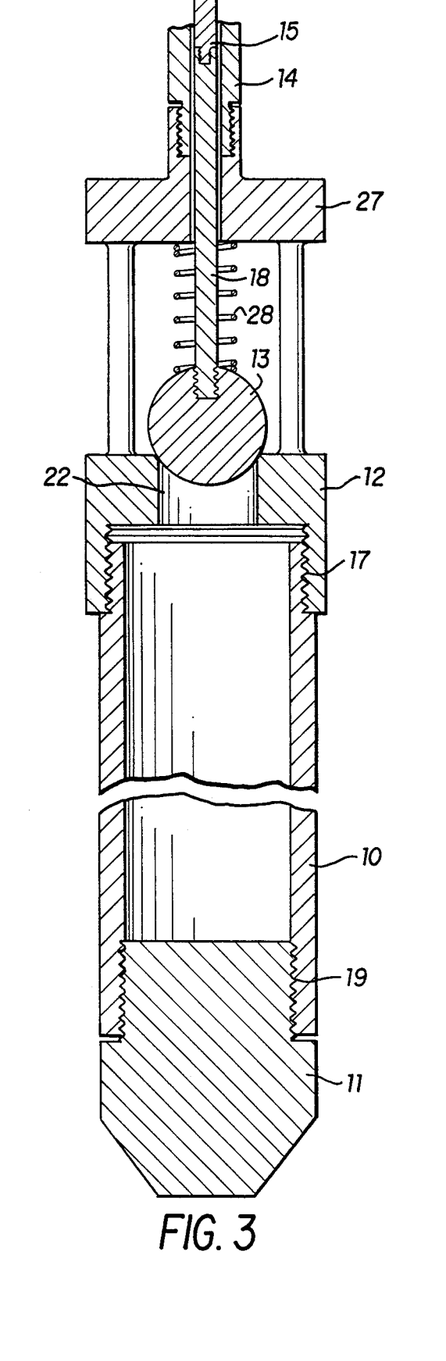
FIG. 3 is a cross-section of the invention illustrating the valve in the closed position.

In FIG. 1 the invention may be seen to be comprised of a container 10, closed at its lower end with an end cap 11 and closed at its upper end with a top cap 12. The top cap further comprises an opening (not shown), a ball valve 13 which covers the opening, a hollow rigid tube 14 for lowering the device into the testing medium, and a rod 15 which is slideably disposed within the hollow tube and connected to the ball valve 13. The rod 15 is raised and lowered by pulling the knob 16 up and down in a vertical orientation. In FIG. 2 it may be more clearly seen that the container 10 is threaded at either end 17 for attachment of the end cap 11 and top cap 12. The threaded feature of the container also allows a multiple number of containers to be joined one to the other for the purpose of taking larger volume samples and to permit each container to be capped separately for maintaining the integrity of the sample contained in each container. To the ball valve 13 is attached a short rod 18 which, as more fully seen in FIG. 3, is connected to the main rod 15 by threaded screw means. The hollow rigid tube 14 is machined with threads at either end for attachment of the tube to the top cap 12, and for attachment, if necessary, of multiple lengths of tubing where, for example, testing may have to be done in a deep well. The knob 16 is similarly detachably attached to the main rod 15 by threaded screw means. As shown by FIG. 2, the entire device may be disassembled for easy transportation, for interchangeability of parts, and for easy cleaning and decontamination.

Figure 4:
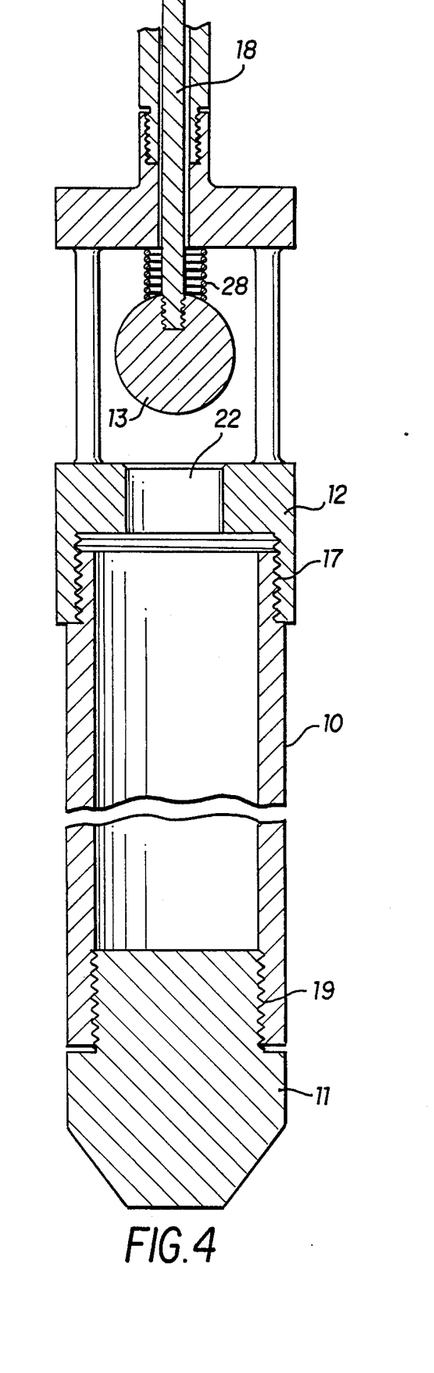
FIG. 4 is a cross-section of the invention illustrating the valve in the open position.

FIG. 3 more fully illustrates how the end cap 11 is attached to the container 10 by threaded screw means 19, and similarly, how the top cap 21 is attached to the container 10 by threaded screw means 17. The top cap is shown to have an opening 22 leading into the container, and the opening is obstructed by the ball valve 13. The ball valve is actuated by the main rod 15 which is connected to the shorter shaft 18 which is connected to the ball valve 13. The main rod 15 is slideably disposed within the hollow tube 14 which is connected to the upper portion 27 of the top cap 12, the two being connected by threaded screw means. The ball valve is maintained against the opening 22 by a spring 28 biased between the ball valve 13 and the upper portion 27 of the top cap 12. In FIG. 4 the rod 18 has been pulled upward in a vertical orientation so as to displace the ball valve 13 from the opening 22 in the top cap. When in the open position, the spring is compressed, and release of the rod 18 will cause the spring to distend again thereby closing the valve against the opening.

Figure 5:
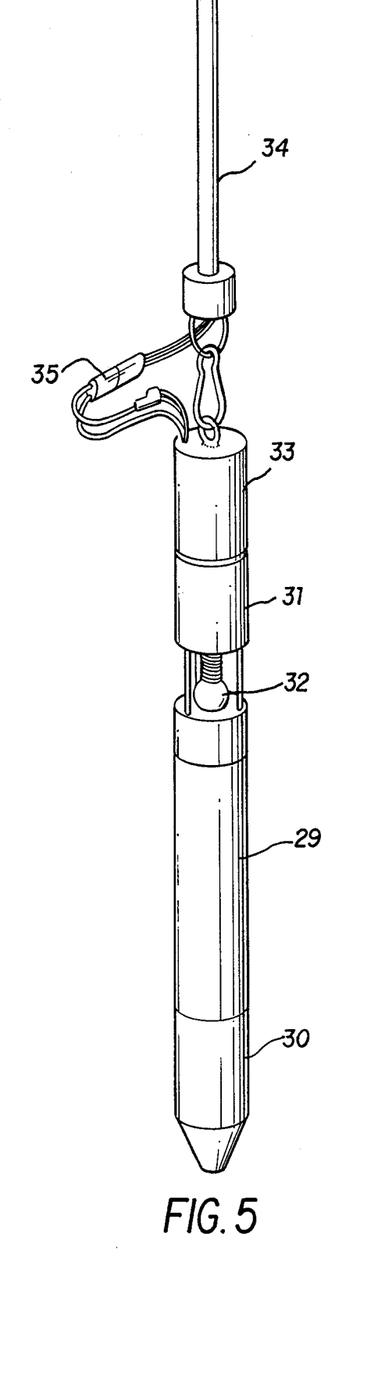
FIG. 5 is a plan view of the invention illustrating the electrically operated valve embodiment.
Figure 6:
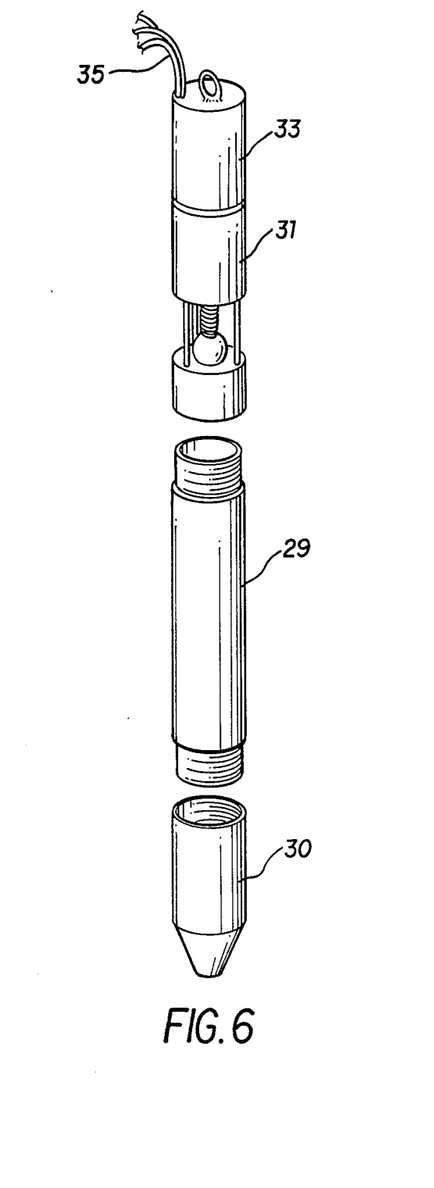
FIG. 6 is a partially exploded plan view of the invention illustrating the electrically operated valve embodiment.

FIG. 5 illustrates an embodiment employing electrical means to acutate the ball valve. The container 29 is again fitted with an end cap 30 and top cap 31 with ball valve 32, but the top cap is also fitted with a solenoid 33 for actuating the valve. The device is lowered into the testing medium by a cable 34 through which the electrical wires 35 run for activating the solenoid 33. In FIG. 6, the container 29 is shown to have threaded ends for attachment of the end cap 30 and top cap 31. The threaded ends, however, also allow the placement of other caps on the ends of the container, or the joining of multiple numbers of containers together.

Figure 7:
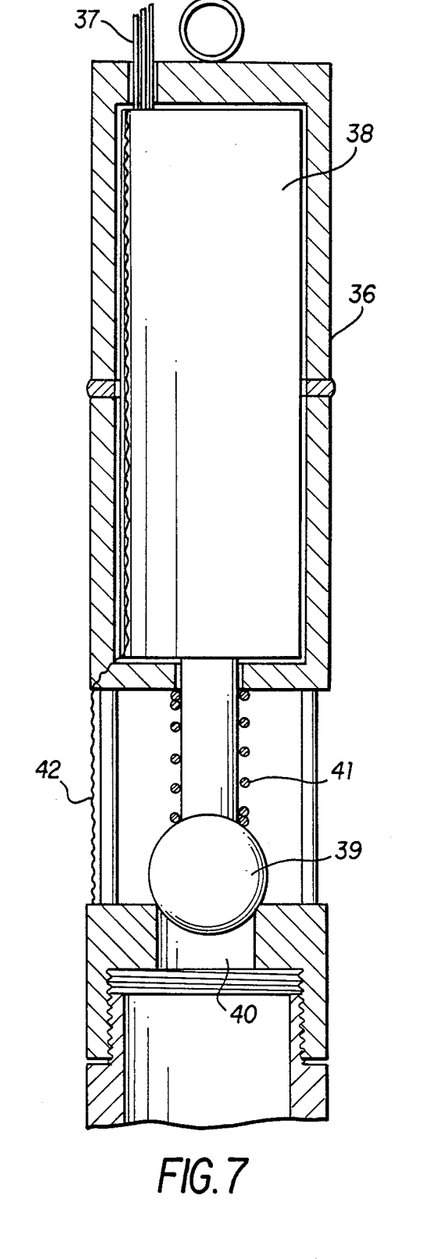
FIG. 7 is a cross-section view of the electrically operated valve in the closed position.
Figure 8:
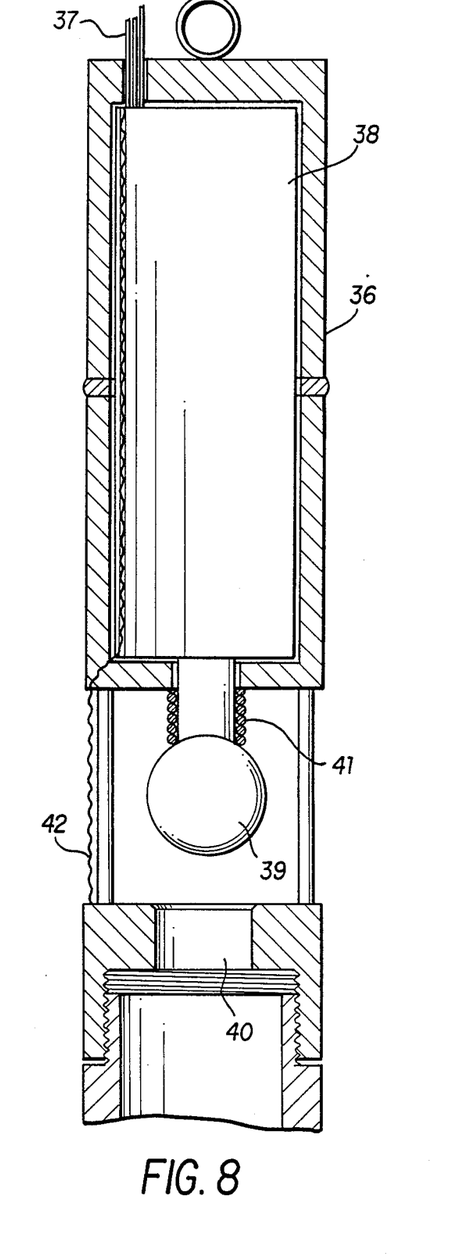
FIG. 8 is a cross-section view of the electrically operated valve in the open position.

FIGS. 7 and 8 show a cross-section of the top cap 36 illustrating entry of the electrical wiring 37 into the top cap which activates the solenoid 38 contained in the top cap 36. The ball valve 39, in the closed position as shown in FIG. 7, rests against the top cap opening 40, and is held in place by a spring 41 biased against the ball valve and the top cap. When activated, the solenoid causes the spring 41 to compress, as shown in FIG. 8, and the ball valve 39 is raised from the opening 40. A well known means such as a monitor means in the form of an electrically conductive wire 42 can be utilized to signal when the ball valve 39 has touched fluid as the container is lowered into the fluid medium to be tested.

Figure 9:
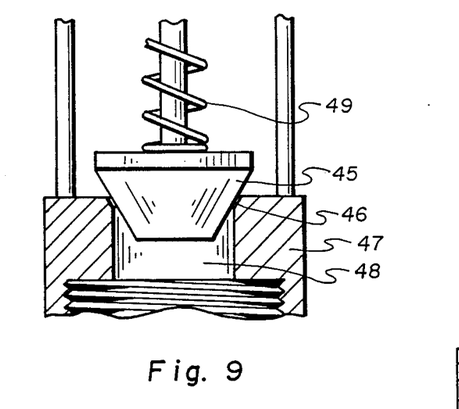
FIG. 9 is a plan view of an alternative embodiment of the valve.
Figure 10:
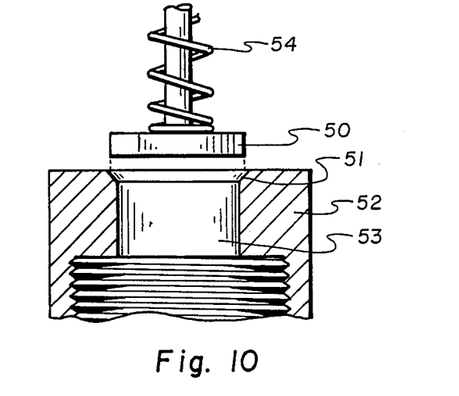
FIG. 10 is a plan view of an alternative embodiment of the valve.

FIG. 9 illustrates an alternative embodiment of a valve 45 which is substantially conically shaped with a truncated end. The valve 45 sits against a valve seat 46 formed in the top cap 47 which obstructs the opening 48 into the container. The valve is maintained in place by a spring 49 biased between the valve and the upper portion of the top cap (not shown). FIG. 10 illustrates another embodiment of a valve 50 which is substantially flattened. The valve 50 sits against a valve seat 51 formed in the top cap 52 which, when the disc is in place as suggested by the dotted lines, obstructs the opening 53 into the container. As with other embodiments, the disc valve is kept in place by a spring 54.

Figure 11:
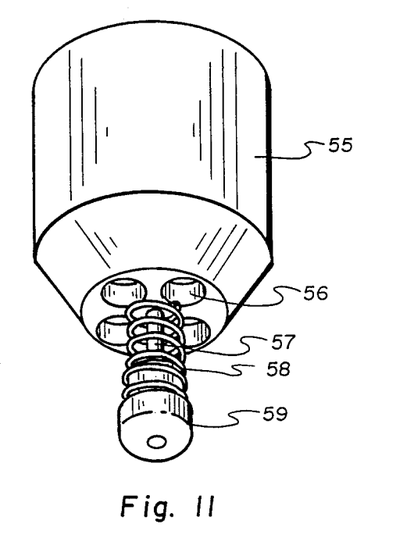
FIG. 11 is a perspective view of the emptiable end cap embodiment.
Figure 12:
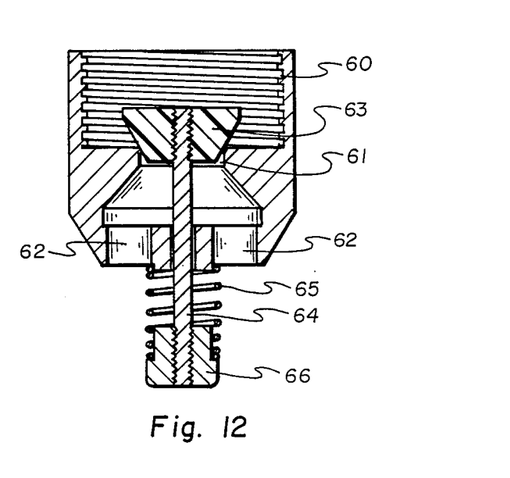
FIG. 12 is a cross-section view of the emptiable end cap in the closed position.
Figure 13:
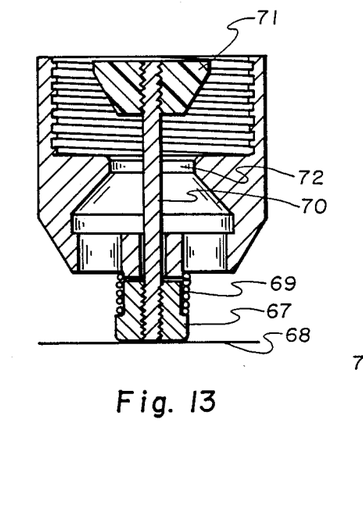
FIG. 13 is a cross-section view of the emptiable end cap in the open position.

An emptiable end cap is illustrated in FIG. 11 which allows the discharging of the contents of the container. In this embodiment, a plurality of holes 56 are located in the bottom of the end cap 55 through which the contents are discharged. Passing vertically through the end cap is a shaft 57 which is connected to a valve (not shown) located within the end cap. The shaft keeps the valve closed against the opening (not shown) by means of a spring 58 biased between the tip 59 and the bottom of the end cap. In FIG. 12 it may be seen that the end cap 60 has an opening 61 which leads out into a plurality of openings 62. A valve 63 obstructs the opening 61. The valve is connected to a shaft 64 which passes vertically through the bottom of the end cap. A spring 65 biased between the bottom of the end cap and a tip 66 keeps the valve in the closed position. As illustrated in FIG. 13, when the tip 67 is pressed against a surface 68, the spring 69 is compressed, the shaft 70 is pushed upwardly, and the valve 71 is displaced from the opening 72 thereby allowing the contents of the container to drain outwardly. When the tip is released from the surface, the spring distends once again, closing the valve against the opening.

Figure 14:
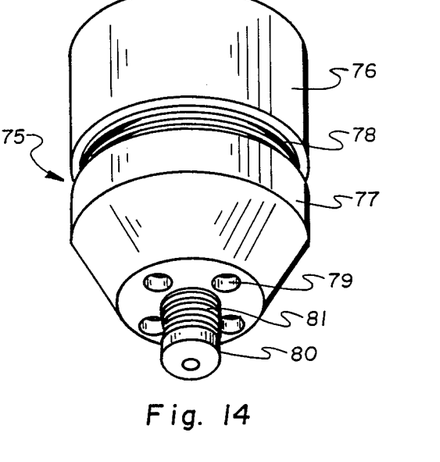
FIG. 14 is a perspective view of the two stage emptiable end cap embodiment shown in the valve-closed position.
Figure 15:
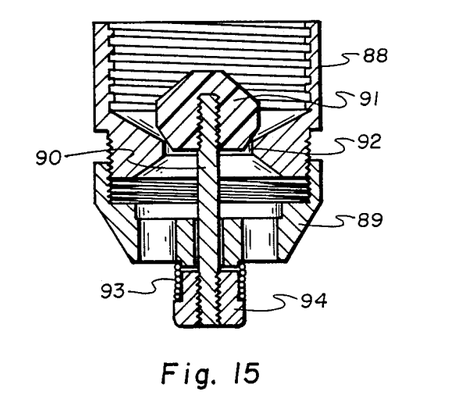
FIG. 15 is a cross-section view of the two stage emptiable end cap in the valve-closed position.
Figure 16:
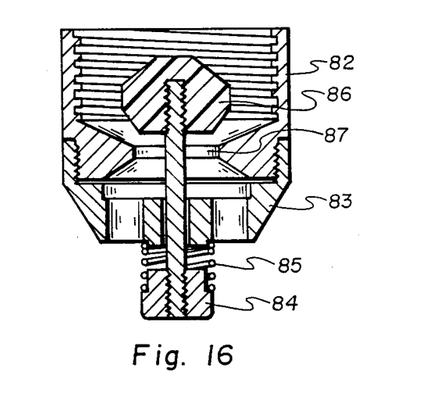
FIG. 16 is a cross-section view of the two stage emptiable end cap in the valve-open position.

In an alternative embodiment, the end cap, generally at 75 in FIG. 14, is comprised of an upper stage 76 and a lower stage 77, the two stages being adjustable in relationship to one another by rotating the stages together or apart via threaded screw means 78. The lower stage contains a plurality of holes 79 through which the contents of the container will pass when the tip 80 is pressed against a surface thereby constricting the spring 81 and releasing a valve (not shown) within the end cap; This action will take place only when the upper and lower stage are adjusted together as illustrated in FIG. 16. In FIG. 16 the upper stage 82 is adjusted to be flush with the lower stage 83. In this configuration, when the tip 84 is pressed against a surface, the spring 85 is free to compress thereby displacing the valve 86 from the opening 87. But when the upper stage 88 is adjusted to its farthest proximity from the lower stage 89, as shown in FIG. 15, the expansion thus created equals the length of the shaft 90 and the valve 91 is forced against the opening 92 and the spring 93 is necessarily compressed. In this configuration, the valve is locked in a closed position. This assures that bumping the tip 94 against a surface will not accidently open the valve thereby releasing the contents of the container. FIG. 14 illustrates how the spring 81 is compressed in the closed position when the upper stage 76 and the lower stage 77 are adjusted to the farthest proximity from each other to lock the valve in place.

While this invention has been described and illustrated herein with respect to preferred embodiments, it is understood that alternative embodiments and substantial equivalents are included within the scope of the invention as defined by the appended claims.

I claim:

1. An apparatus for taking samples of liquid and semi-liquid substances comprising, in combination:
    a cylindrical hollow tube with screw threads at either end for selectively attaching end caps or attaching other tubes sequentially;

a first cap attached to one end of said hollow tube by means of screw threads which interfacingly engage with said threads of said hollow tube;

a second cap attached to said other end of said hollow tube by means of screw threads which interfacingly engage with said threads of said hollow tube, said second cap having an opening therein sealed, when in the closed position, by a ball valve;

an actuating means attached to said ball valve for releasing said ball valve from said opening in said second cap.

2. An apparatus for taking samples of liquid and semi-liquid substances comprising, in combination:

a hollow container having two opposing ends and screw threads at both ends of said container;

a first cap attached to one end of said hollow container;

a second cap attached to an opposite end of said hollow container, said second cap having an opening therein through which sample material may pass to the inside of said container;

a valve which sits against said opening when in the closed position;

an actuating means attached to said valve for opening and closing said valve, said screw threads allowing for selectively attaching any two of said first cap, said second cap, or sequential numbers of hollow containers.

3. An apparatus as set forth in claim 2 in which said container is substantially cylindrical.

4. An apparatus as set forth in claim 2 in which said container is manufactured of a material substantially impermeable to the material being sampled.

5. An apparatus as set forth in claim 2 in which said valve is a ball.

6. An apparatus as set forth in claim 2 in which said valve is a flattened disc.

7. An apparatus as set forth in claim 2 in which said valve is of conical shape with a truncated end.

8. An apparatus as set forth in claim 2 in which said actuating means comprises a hollow shaft attached to said second cap by screw threads, a rod slideably disposed through said hollow shaft, one end of said rod being attached to said valve and the other end of said rod extending above said hollow shaft, and a spring biased against said valve and said second cap for seating of said valve against said opening in said second cap.

9. An apparatus as set forth in claim 2 in which said actuating means comprises an electronic solenoid attached to said valve.

10. An apparatus as set forth in claim 2 in which said first cap further comprises an opening leading from said container to a plurality of outlets, a valve which blocks said opening, said valve being actuated by a rod passing vertically through said first cap, one end of said rod being attached to said valve, the other end of said rod being attached to a tip external to said first cap, and a spring biased against said tip and said first cap for maintaining said valve in a closed position.

11. An apparatus as set forth in claim 2 in which said first cap comprises a first stage being comprised of a hollow tube container and an opening, a truncated second stage, said second stage having a plurality of outlets therein, a rod passing vertically through said first and second stages of said first cap, one end of said rod being attached to a valve which sits against said opening thereto of said hollow tube container in said first stage and the other end of said rod being attached to a tip, a spring biased against said tip and the bottom surface of said second stage, and said first stage and said second stage being integrally attached by threaded screw means which allows said first stage to be separated from said second stage within a specified range with the result that said valve is forced in contact with said opening of said hollow tube container thereby locking said valve in place.

12. An apparatus as set forth in class 2 which further comprises a monitor means for detecting when said apparatus has reached the surface of the testing medium.

* * * * *

UNITED STATES PATENT AND TRADEMARK OFFICE
CERTIFICATE OF CORRECTION

PATENT NO. : 4,949,582
DATED : August 21, 1990
INVENTOR(S) : Arthur R. Vollweiler It is certified that error appears in the above-identified patent and that said Letters Patent is hereby corrected as shown below:

In The Abstract, on line 3, delete "cat", should be --cap--.

Signed and Sealed this

Third Day of December, 1991

Attest:

HARRY F. MANBECK, JR.

Attesting Officer

Commissioner of Patents and Trademarks